| United States Patent [19] | [11] Patent Number: 4,874,884 |
|---|---|
| McKinney et al. | [45] Date of Patent: Oct. 17, 1989 |

[54] PROMOTER SYNERGISM IN PENTENENITRILE HYDROCYANATION

[75] Inventors: Ronald J. McKinney, Wilmington, Del.; Robert B. Osborne, Orange, Tex.

[73] Assignee: E. I. Du Pont de Nemours and Company, Wilmington, Del.

[21] Appl. No.: 310,411

[22] Filed: Feb. 14, 1989

Related U.S. Application Data

[63] Continuation-in-part of Ser. No. 176,241, Mar. 31, 1988.

[51] Int. Cl.⁴ .......................................... C07C 120/02
[52] U.S. Cl. ................................................ 558/338
[58] Field of Search .................................... 558/338

[56] References Cited

U.S. PATENT DOCUMENTS

| 2,571,099 | 10/1951 | Arthur et al. | 260/465.3 |
| 3,496,215 | 2/1970 | Drinkard et al. | 260/465.8 |
| 3,496,217 | 2/1970 | Drinkard et al. | 260/465.8 |
| 3,496,218 | 2/1970 | Drinkard et al. | 260/465.8 |
| 3,852,325 | 12/1974 | King | 260/465.9 |
| 3,903,120 | 9/1975 | Shook, Jr. et al. | 260/439 |
| 3,925,445 | 12/1975 | King et al. | 260/465 |
| 4,774,353 | 9/1988 | Hall et al. | 558/335 |

*Primary Examiner*—Joseph P. Brust

[57] ABSTRACT

Process for producing adiponitrile by the zerovalent nickel catalyzed hydrocyanation of pentenenitriles is improved by using a synergistic combination of promoters selected in accordance with the reaction kinetics of the synthesis.

6 Claims, No Drawings

PROMOTER SYNERGISM IN PENTENENITRILE HYDROCYANATION

RELATED APPLICATION

This application is a continuation-in-part of copending application Ser. No. 07/176,241, filed Mar. 31, 1988.

FIELD OF INVENTION

This invention concerns an improved process for producing adiponitrile (ADN) by the zerovalent nickel catalyzed hydrocyanation of pentenenitriles (PN), wherein the improvement comprises utilizing a combination of two catalyst promoters specially selected on the basis of the reaction kinetics of the synthesis.

BACKGROUND OF THE INVENTION

The preparation of dinitriles, such as ADN, from mononitriloolefins, such as PN, utilizing zerovalent nickel catalysts with or without a catalyst promoter is widely practiced in the art. The preparation of ADN from PN is of particular interest because ADN is an intermediate used in the production of hexamethylenediamine which is in turn used to produce polyhexamethyleneadipamide, a commercial polyamide useful in forming fibers, films and molded articles.

U.S. Pat. No. 2,571,099, issued on Oct. 16, 1951 to Paul Arthur, Jr. et al. discloses the use of nickel carbonyl with or without the addition of a tertiary aryl phosphine or arsine. This process produces a relatively high percentage of undesirable polymeric products when applied to nonconjugated olefinic starting materials and a relatively poor yield in all cases.

U.S. Pat. No. 3,496,215, issued on Feb. 17, 1970 to W. C. Drinkard et al., discloses an improvement in nickel-catalyzed hydrocyanation wherein triarylphosphite ligands are utilized and carbonyl ligands are eliminated, thereby dramatically reducing polymer formation and generally increasing yield to desirable nitrile products.

The teaching of the use of a promoter in the hydrocyanation reaction appears in U.S. Pat. No. 3,496,217 issued on Feb. 17, 1970 to W. C. Drinkard et al. This patent discloses an improvement in hydrocyanation using a promoter selected from a large number of metal cation compounds with a variety of anions as catalyst promoters. More particularly, the patent discloses as a promoter a cation of zinc, cadmium, beryllium, aluminum, gallium, indium, silver, titanium, zirconium, hafnium, germanium, tin, vanadium, niobium, scandium, chromium, molybdenum, tungsten, manganese, rhenium, palladium, thorium, erbium, iron and cobalt, or mixtures thereof. Preferred anions are halide, i.e., fluoride, chloride, bromide, and iodide; anions of lower fatty acids of from 2 to 7 carbon atoms, $HPO_3^{-2}$, $H_2PO_2^-$, $CF_3COO^-$, $OSO_2C_7F_{15}^-$, and $SO_4^{-2}$, etc. The known organometallic compounds $(C_2H_5)_3Al_2Cl_3$, and $C_2H_5AlCl_2$ are also disclosed as promoters.

U.S. Pat. No. 3,496,218 issued on Feb. 17, 1970 to C. W. Drinkard discloses a nickel hydrocyanation catalyst promoted with various boron-containing compounds, including triphenylboron and alkali metal borohydrides.

U.S. Pat. No. 3,925,445 issued on Dec. 9, 1975 to C. M. King et al. discloses zerovalent nickel hydrocyanation catalysts promoted with metal halides and organoboron compounds.

U.S. Pat. No. 3,852,325 issued on Dec. 3, 1974 to C. M. King teaches that along with production of 3-pentenenitrile (3PN) in the hydrocyanation of butadiene there is also obtained varying amounts of cis- and trans-2-pentenenitriles (C-2PN and T-2PN) and that these 2-pentenenitriles are found to be detrimental to catalyst efficiency in the hydrocyanation of 3PN or 4-pentenenitrile (4PN) to adiponitrile (ADN). The patentee also teaches that T-2PN cannot be removed satisfactorily from a mixture of pentenenitriles by fractional distillation, for example, because its boiling point is too close to that of other pentenenitriles such as 3PN or 4PN. Isomerizing T-2PN to the more volatile C-2PN which in turn can be removed from the reaction mixture by fractional distillation is discussed.

U.S. Pat. No. 4,774,353 issued on Sept. 27, 1988, discloses a process for the preparation of dinitriles, e.g., ADN, from unsaturated nitriles, e.g., PN, in the presence of a zerovalent nickel catalyst and a triorganotin catalyst promoter having the general formula

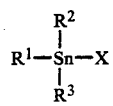

wherein $R^1$, $R^2$ and $R^3$ are the same or different and are selected from groups consisting of alkyl and substituted aryl groups of 6 to 16 carbon atoms. One or more of the substituent groups in the substituted alkyl and aryl groups may be selected from fluoro or alkoxy groups having 1 to 8 carbon atoms, trialkylsilyl groups with alkyls having 1 to 6 carbon atoms, cyanoalkyl groups having 1 to 20 carbon atoms, and sulfonato. The anion X is a non-nucleophilic ion, the conjugate acid of which has a $pK_a$ less than about 4.

SUMMARY OF THE INVENTION

The present invention is an improvement in the process for producing adiponitrile by the addition of hydrogen cyanide to pentenenitriles in the presence of a zerovalent nickel catalyst, and catalyst promoter, the improvement comprising conducting the process in the presence of a combination of two Lewis acid promoters, $LA_A$ and $LA_B$, wherein the rate constant for the rate of isomerization of 3-pentenenitrile to 4-pentenenitrile, $k_1$, in the presence of the first Lewis acid promoter, $LA_A$, is greater than $k_1$ in the presence of the second Lewis acid promoter, $LA_B$, and wherein the rate constant for the rate of hydrocyanation of 4-pentenenitrile to adiponitrile, $k_2$, in the presence of $LA_B$ is greater than $k_2$ in the presence of $LA_A$.

While a wide variety of Lewis acid promoters known in the art and described therein are useful when selected in accordance with this invention, preferable promoter combinations include those in which $LA_A$ is $BPh_3$ and $LA_B$ is one selected from $CoCl_2$, $ZnI_2$, $AlCl_3$, $AlRCl_2$, $AlR_2Cl$, $R_2SnX$, $Ar_3SnY$, where R is an alkyl group of from 1 to 15 carbons, Ar is a substituted or non-substituted aryl group of from 1 to 20 carbons, X is selected from $SbF_6$, $PF_6$, $BF_4$, or $CF_3SO_3$, and Y is selected from $SbF_6$, $PF_6$, $BF_4$, $CF_3SO_3$, or $Ph_3BCN$, as well as those in which $LA_A$ is one selected from $CoCl_2$, $ZnI_2$, $Ph_3SnPh_3BCN$, or $Ph_3SnZnCl_2CN$ and $LA_B$ is one selected from $AlCl_3$, $AlRCl_2$, $AlR_2Cl$, $R_3SnX'$, $Ar_3SnY'$, where R is an alkyl group of from 1 to 15 carbons, Ar is a substituted or non-substituted aryl group of from 1 to 20 carbons, X' is selected from $SbF_6$, $PF_6$, or $BF_4$, and Y' is selected from $SbF_6$, $PF_6$, $BF_4$, $CF_3SO_3$, and those in which $LA_A$ is $ZnCl_2$ and $LA_B$ is one selected from $AlCl_3$, $AlRCl_2$, $AlR_2Cl$, $R_3SnY'$, $Ar_3SnY'$, where R is an alkyl group of from 1 to 15 carbons, Ar is a substituted or non-substituted aryl group of from 1 to 20 carbons, X' is selected from $SbF_6$, $PF_6$, or $BF_4$, and Y' is selected from $SbF_6$, $PF_6$, $BF_4$, $CF_3SO_3$, and those in which $LA_A$ is selected from $AlR_2Cl$ or $CoI_2$ and $LA_B$ is $Ar_3SnY'$ where R is an alkyl group of from 1 to 15 carbons, Ar is a substituted or non-substituted aryl group of from 1 to 20 carbons, and Y' is selected from $SbF_6$, $PF_6$, $BF_4$, $CF_3SO_3$.

Use of a combination of promoters in accordance with this invention increases catalyst activity to an extent that reduces the total amount of promoter and/or catalyst fed to the system and minimizes the yield of undesirable 2PN, a well-known cause of yield loss and catalyst inhibition.

Furthermore, because undesirable 2PN yield is reduced, conversion may be dramatically increased and recycle reduced. Because activity is greater, the steady state concentration of HCN may be kept lower, resulting in less catalyst degradation and, therefore, a reduction in the amount of solids in the process streams.

DETAILED DESCRIPTION OF THE INVENTION

In the zerovalent nickel catalyzed hydrocyanation of PN to produce ADN, the synthesis proceeds as follows:

(1) 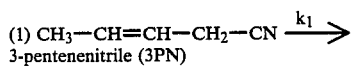
3-pentenenitrile (3PN)

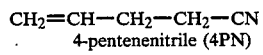
4-pentenenitrile (4PN)

Where $k_1$ = rate constant for reaction (1)

(2) 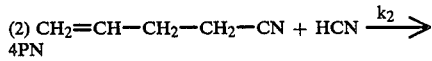

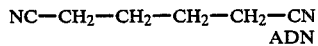
ADN

Where $k_2$ = rate constant for reaction (2)

In accordance with this invention, it was discovered that some promoters, e.g. $BPh_3$, are better for promoting the isomerization of reaction (1), whereas other promoters, e.g. $Ph_3SnO_3SCF_3$, are relatively more active for promoting the hydrocyanation of reaction (2). A selected combination of such promoters leads to a higher steady state concentration of 4PN than the more active hydrocyanation promoter of reaction (2) would normally encounter in single promoter systems or in systems containing incorrectly selected promoter combinations. Thus, combinations of promoters in accordance with this invention provides a synergistic increase in the overall synthesis rate.

The initial rate of isomerization of 3PN to 4PN, reaction (1), is defined by the rate expression $$d[4PN]/dt = k_1 \times [3PNH]$$

wherein $k_1$ includes the concentrations of all catalytic species, such as $NiL_4$, L, LA and HCN, whereas the initial rate of hydrocyanation of 4PN to ADN, reaction (2) is defined by the rate expression $$d[ADN]/dt = k_2 \times [4PN]$$

wherein $k_2$ includes the concentrations of all catalytic species, such as $NiL_4$, L, LA and HCN, wherein LA = Lewis acid promoter and L = neutral ligand.

Designating two different Lewis acids as $LA_A$ and $LA_B$, effective combinations of Lewis acids will exhibit rate synergism when:

$$k_1(LA_A) > k_1(LA_B) \text{ and } k_2(LA_B) > k_2(LA_A).$$

The rate constants $k_1$ and $k_2$ can be determined for a selected Lewis acid by contacting a solution of zerovalent nickel catalyst in 3PN with a solution of the Lewis acid promoter in 3PN, heating the resulting solution in an inert atmosphere, to a temperature from about 0° C. to about 75° C., injecting HCN into the heated solution to commence the hydrocyanation, removing aliquots of the resulting solution at measured time intervals, and analyzing the aliquots for the concentration of the components of the aliquot. The analysis results in a concentration versus time profile of the components of the aliquots, in particular 4PN and ADN.

Kinetic modeling using an interactive GEAR integration computer program (GIT) allowed the extraction of the desired rate constants on the basis of the concentration versus time date. (See Weigert, F. J. Computers in Chemistry, Volume 11, page 273, 1987; GIT is available through Quantum Chemistry Program Exchange, QCPE, Department of Chemistry, Indiana University, Bloomington, Ind.; QCPE #552 (VAX version); QCMP #022 (PC version); ref. QCPE Bulletin Vol. 6, No. 4, pgs 136, 141). The following chemical equations were used in the kinetic modeling procedure:

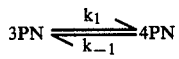

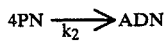

where $NiL_4$ 3PN and 4PN are 3- and 4-pentenenitriles and ADN is adiponitrile.

The catalysts employed for hydrocyanation are zerovalent nickel (Ni(0)) compounds free of carbon monoxide which may be preformed or prepared in situ and include nickel compounds containing ligands such as alkyl or aryl groups (either of which groups can contain up to 18 carbon atoms) phosphines, arsines, stibines, phosphites, arsenites, stibites, and mixtures thereof.

An especially preferred group of these Ni(0) compounds have the general structure:

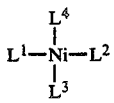

where $L^1$, $L^2$, $L^3$ and $L^4$ are neutral ligands which may be the same or different and have the formula P(XYZ) wherein X and Y are selected from the class consisting of R and OR, and Z has the formula OR, wherein the three R's may be the same or different, and wherein R is selected from the class consisting of alkyl and aryl groups containing up to 18 carbon atoms with aryl.

A particularly preferred group within the foregoing zerovalent nickel catalysts are those found in U.S. Pat. No. 3,903,120 issued on Sept. 2, 1975 which can be described by the general formula NiL4 where L is a neutral ligand such as a triaryl phosphite of the formula P(OAr)$_3$ wherein Ar is an aryl group of up to 18 carbon atoms. Illustrative of the aryl groups are methoxyphenyl, tolyl, xylyl and phenyl. Meta- and para-tolyl and mixtures thereof are the preferred aryl groups. Excess ligand can be employed.

The promoters useful in the practice of this invention can be selected in combination in accordance with this invention from a wide variety of promoters known in the art. Particularly useful are those described in U.S. Pat. Nos. 3,496,217, 3,496,218, 3,925,445 and 4,774,353. Of these promoters, BPh$_3$, ZnCl$_2$, Ph$_3$SnO$_3$SCF$_3$, Ph$_3$SnPh$_3$BCN and C$_{12}$H$_{25}$AlCl$_2$ in combinations selected in accordance with the invention are highly effective. Especially preferred are combinations of BPh$_3$ with one of Ph$_3$SnO$_3$SCF$_3$, Ph$_3$SnPh$_3$BCN and C$_{12}$H$_{25}$AlCl$_2$.

EXAMPLE A

Determination of Rate Constants

A nickel catalyst mixture was prepared by dissolving tetrakis(tri-para-tolylphosphite)nickel(0) (0.625 g; 0.426 mmol) and tri-para-tolylphosphite (1.00 mL; 1.15 g; 3.26 mmol) in 3-pentenenitrile (3PN) (49 mL).

For each LA promoter tested (Shown in Table 1), a promoter mixture was prepared by dissolving sufficient promoter in 4.6 mL of 3PN to result in a 0.41M solution of promoter.

A 4.0 mL aliquot of the nickel catalyst solution was treated with 0.030 mL of the promoter solution, sealed in a 5 mL vial under nitrogen with a septum cap and heated in a thermostated oil bath at 52° C. After temperature equilibration, liquid HCN (0.025 mL) was injected through the septum. Aliquots (0.015 mL) of the reaction mixture were removed by syringe at measured time intervals and quenched by dilution in air saturated acetone (1.5 mL). Capillary gas chromatographic analysis (25 m Carbowax) of these samples resulted in a concentration versus time profile of the products of the hydrocyanation, in particular 4PN and ADN.

These data were input to the iterative GEAR program (GIT) to give the values for $k_1$ and $k_2$ shown for the Lewis acids in Table 1.

TABLE 1

| Lewis Acid Promoter | $k_1 \times 10^4$ (sec$^{-1}$) | $k_2 \times 10^3$ (sec$^{-1}$) |
| --- | --- | --- |
| BPh$_3$ | 5.79 | 2.12 |
| ZnCl$_2$ | 2.12 | 2.03 |
| Ph$_3$SnO$_3$SCF$_3$ | 1.25 | 8.69 |
| Ph$_3$SnO$_3$SC$_6$H$_4$CH$_3$ | 0.41 | 1.35 |
| Ph$_3$SnPh$_3$BCN | 3.96 | 2.90 |
| (c-C$_6$H$_{11}$)$_3$SnO$_3$SCF$_3$ | 0.48 | 2.32 |

TABLE 2

| Synergistic Combinations | | $k_1 \times 10^4$ (sec$^{-1}$) | $k_2 \times 10^3$ (sec$^{-1}$) |
| --- | --- | --- | --- |
| BPh$_3$ | Ph$_3$SnO$_3$SCF$_3$ | 7.92 > 1.72 | 2.90 < 11.88 |
| BPh$_3$ | Ph$_3$SnPh$_3$BCN | 7.92 > 5.41 | 2.90 < 3.96 |
| BPh$_3$ | (c-C$_6$H$_{11}$)$_3$SnO$_3$SCF$_3$ | 7.92 > .66 | 2.90 < 3.17 |
| ZnCl$_2$ | Ph$_3$SnO$_3$SCF$_3$ | 2.90 > 1.72 | 2.77 < 11.88 |
| ZnCl$_2$ | (c-C$_6$H$_{11}$)$_3$SnO$_3$SCF$_3$ | 2.90 > .66 | 2.77 < 3.17 |
| Ph$_3$SnPh$_3$BCN | Ph$_3$SnO$_3$SCF$_3$ | 5.41 > 1.72 | 3.96 < 11.88 |

EXAMPLE B

The rate constants for a second larger set of promoters was determined under somewhat different conditions. Where the same promoters are found in both Example A and B, the differences in $k_1$ and $k_2$ result from changes in concentrations of catalytic species such as NiL4 and L.

Nickel catalyst mixtures were prepared by dissolving tetrakis(tri-para-tolylphosphite)nickel(0) (0.30 g; 0.204 mmol) and tri-para-tolylphosphite (2.00 cc; 6.53 mmol) in 3-pentenenitrile (39 mL).

For each promoter tested, sufficient sample was dissolved directly in a 4.0 mL aliquot of catalyst mixture to provide a concentration of promoter of 0.003 mol/liter, or as in A above, was predissolved and added by syringe to provide the same concentration. The 4.0 mL aliquot of catalyst mixture containing the promoter was sealed in a 5 mL vial under nitrogen with a septum cap and equilibrated in a thermostated oil bath at 50° C. Liquid HCN (0.025 mL) was injected through the septum. Analysis was carried out in a manner similar to that described in Example A. The results of the kinetic analysis are provided in Table 3 and synergistic combinations are provided in Table 4.

TABLE 3

| Lewis Acid Promoter | $k_1 \times 10^4$ (sec$^{-1}$) | $k_2 \times 10^3$ (sec$^{-1}$) |
| --- | --- | --- |
| BPh$_3$ | 2.16 | 0.75 |
| CoCl$_2$ | 0.86 | 1.42 |
| Ph$_3$SnCNBPh$_3$ | 0.71 | 1.08 |
| ZnI$_2$ | 0.58 | 0.88 |
| Ph$_3$SnCNZnCl$_2$ | 0.51 | 0.49 |
| (iPr)$_3$SnSbF$_6$ | 0.50 | 2.20 |
| (cC$_6$H$_{11}$)$_3$SnSbF$_6$ | 0.43 | 2.69 |
| ZnCl$_2$ | 0.39 | 0.44 |
| (neC$_5$H$_{11}$)$_3$SnSbF$_6$ | 0.37 | 2.84 |
| Et$_3$SnSbF$_6$ | 0.31 | 2.54 |
| (iBu)$_3$SnSbF$_6$ | 0.29 | 2.65 |
| AlEt$_2$Cl | 0.26 | 2.39 |
| Me$_3$SnSbF$_6$ | 0.24 | 3.11 |
| Ph$_3$SnO$_3$SCF$_3$ | 0.20 | 3.89 |
| FeCl$_3$ | 0.15 | 0.14 |
| CoI$_2$ | 0.14 | 0.38 |
| CrCl$_2$ | 0.14 | 0.11 |
| (FC$_6$H$_4$)$_3$SnSbF$_6$ | 0.13 | 3.90 |
| Ph$_3$SnSbF$_6$ | 0.11 | 2.57 |
| Co(NO$_3$)$_2$.6H$_2$O | 0.09 | 0.11 |
| CrCl$_3$ | 0.08 | 0.10 |
| AlEt$_3$ | 0.07 | 0.10 |
| VCl$_3$ | 0.07 | 0.07 |
| TiCl$_3$ | 0.06 | 0.16 |
| FeCl$_2$.4H$_2$O | 0.06 | 0.06 |
| ZnMe$_2$ | 0.04 | 0.08 |
| ZnPh$_2$ | 0.03 | 0.07 |
| AlEtCl$_2$ | 0.01 | 1.88 |
| AlCl$_3$ | 0.00 | 1.50 |

TABLE 4

| | Synergistic Combinations | $k_1 \times 10^4$ (sec$^{-1}$) | $k_2 \times 10^3$ (sec$^{-1}$) |
|---|---|---|---|
| BPh$_3$ | CoCl$_2$ | 2.16 > .86 | .75 < 1.42 |
| BPh$_3$ | Ph$_3$SnCNBPh$_3$ | 2.16 > .71 | .75 < 1.08 |
| BPh$_3$ | ZnI$_2$ | 2.16 > .58 | .75 < .88 |
| BPh$_3$ | (iPr)$_3$SnSbF$_6$ | 2.16 > .50 | .75 < 2.20 |
| BPh$_3$ | (c-C$_6$H$_{11}$)$_3$SnSbF$_6$ | 2.16 > .43 | .75 < 2.69 |
| BPh$_3$ | (neC$_5$H$_{11}$)$_3$SnSbF$_6$ | 2.16 > .37 | .75 < 2.84 |
| BPh$_3$ | Et$_3$SnSbF$_6$ | 2.16 > .31 | .75 < 2.54 |
| BPh$_3$ | (iBu)$_3$SnSbF$_6$ | 2.16 > .29 | .75 < 2.65 |
| BPh$_3$ | AlEt$_2$Cl | 2.16 > .26 | .75 < 2.39 |
| BPh$_3$ | Me$_3$SnSbF$_6$ | 2.16 > .24 | .75 < 3.11 |
| BPh$_3$ | Ph$_3$SnO$_3$SCF$_3$ | 2.16 > .20 | .75 < 3.89 |
| BPh$_3$ | (FC$_6$H$_4$)$_3$SnSbF$_6$ | 2.16 > .13 | .75 < 3.90 |
| BPh$_3$ | Ph$_3$SnSbF$_6$ | 2.16 > .11 | .75 < 2.57 |
| BPh$_3$ | AlEtCl$_2$ | 2.16 > .01 | .75 < 1.88 |
| BPh$_3$ | AlCl$_3$ | 2.16 > .00 | .75 < 1.50 |
| CoCl$_2$ | (iPr)$_3$SnSbF$_6$ | .86 > .50 | 1.42 < 2.20 |
| CoCl$_2$ | (cC$_6$H$_{11}$)$_3$SnSbF$_6$ | .86 > .43 | 1.42 < 2.69 |
| CoCl$_2$ | (neC$_5$H$_{11}$)$_3$SnSbF$_6$ | .86 > .37 | 1.42 < 2.84 |
| CoCl$_2$ | Et$_3$SnSbF$_6$ | .86 > .31 | 1.42 < 2.54 |
| CoCl$_2$ | (iBu)$_3$SnSbF$_6$ | .86 > .29 | 1.42 < 2.65 |
| CoCl$_2$ | AlEt$_2$Cl | .86 > .26 | 1.42 < 2.39 |
| CoCl$_2$ | Me$_3$SnSbF$_6$ | .86 > .24 | 1.42 < 3.11 |
| CoCl$_2$ | Ph$_3$SnO$_3$SCF$_3$ | .86 > .20 | 1.42 < 3.89 |
| CoCl$_2$ | (FC$_6$H$_4$)$_3$SnSbF$_6$ | .86 > .13 | 1.42 < 3.90 |
| CoCl$_2$ | Ph$_3$SnSbF$_6$ | .86 > .11 | 1.42 < 2.57 |
| CoCl$_2$ | AlEtCl$_2$ | .86 > .01 | 1.42 < 1.88 |
| CoCl$_2$ | AlCl$_3$ | .86 > .00 | 1.42 < 1.50 |
| Ph$_3$SnCNBPh$_3$ | (iPr)$_3$SnSbF$_6$ | .71 > .50 | 1.08 < 2.20 |
| Ph$_3$SnCNBPh$_3$ | (cC$_6$H$_{11}$)$_3$SnSbF$_6$ | .71 > .43 | 1.08 < 2.69 |
| Ph$_3$SnCNBPh$_3$ | (neC$_5$H$_{11}$)$_3$SnSbF$_6$ | .71 > .37 | 1.08 < 2.84 |
| Ph$_3$SnCNBPh$_3$ | Et$_3$SnSbF$_6$ | .71 > .31 | 1.08 < 2.54 |
| Ph$_3$SnCNBPh$_3$ | (iBu)$_3$SnSbF$_6$ | .71 > .29 | 1.08 < 2.65 |
| Ph$_3$SnCNBPh$_3$ | AlEt$_2$Cl | .71 > .26 | 1.08 < 2.39 |
| Ph$_3$SnCNBPh$_3$ | Me$_3$SnSbF$_6$ | .71 > .24 | 1.08 < 3.11 |
| Ph$_3$SnCNBPh$_3$ | Ph$_3$SnO$_3$SCF$_3$ | .71 > .20 | 1.08 < 3.89 |
| Ph$_3$SnCNBPh$_3$ | (FC$_6$H$_4$)$_3$SnSbF$_6$ | .71 > .13 | 1.08 < 3.90 |
| Ph$_3$SnCNBPh$_3$ | Ph$_3$SnSbF$_6$ | .71 > .11 | 1.08 < 2.57 |
| Ph$_3$SnCNBPh$_3$ | AlEtCl$_2$ | .71 > .01 | 1.08 < 1.88 |
| Ph$_3$SnCNBPh$_3$ | AlCl$_3$ | .71 > .00 | 1.08 < 1.50 |
| ZnI$_2$ | (iPr)$_3$SnSbF$_6$ | .58 > .50 | .88 < 2.20 |
| ZnI$_2$ | (cC$_6$H$_{11}$)$_3$SnSbF$_6$ | .58 > .43 | .88 < 2.69 |
| ZnI$_2$ | (neC$_5$H$_{11}$)$_3$SnSbF$_6$ | .58 > .37 | .88 < 2.84 |
| ZnI$_2$ | ET$_3$SnSbF$_6$ | .58 > .31 | .88 < 2.54 |
| ZnI$_2$ | (iBu)$_3$SnSbF$_6$ | .58 > .29 | .88 < 2.65 |
| ZnI$_2$ | AlEt$_2$Cl | .58 > .26 | .88 < 2.39 |
| ZnI$_2$ | Me$_3$SnSbF$_6$ | .58 > .24 | .88 < 3.11 |
| ZnI$_2$ | Ph$_3$SnO$_3$SCF$_3$ | .58 > .20 | .88 < 3.89 |
| ZnI$_2$ | (FC$_6$H$_4$)$_3$SnSbF$_6$ | .58 > .13 | .88 < 3.90 |
| ZnI$_2$ | Ph$_3$SnSbF$_6$ | .58 > .11 | .88 < 2.57 |
| ZnI$_2$ | AlEtCl$_2$ | .58 > .01 | .88 < 1.88 |
| ZnI$_2$ | AlCl$_3$ | .58 > .00 | .88 < 1.50 |
| Ph$_3$SnCNZnCl$_2$ | (iPr)$_3$SnSbF$_6$ | .51 > .50 | .49 < 2.20 |
| Ph$_3$SnCNZnCl$_2$ | (cC$_6$H$_{11}$)$_3$SnSbF$_6$ | .51 > .43 | .49 < 2.69 |
| Ph$_3$SnCNZnCl$_2$ | (neC$_5$H$_{11}$)$_3$SnSbF$_6$ | .51 > .37 | .49 < 2.84 |
| Ph$_3$SnCNZnCl$_2$ | ET$_3$SnSbF$_6$ | .51 > .31 | .49 < 2.54 |
| Ph$_3$SnCNZnCl$_2$ | (iBu)$_3$SnSbF$_6$ | .51 > .29 | .49 < 2.65 |
| Ph$_3$SnCNZnCl$_2$ | AlEt$_2$Cl | .51 > .26 | .49 < 2.39 |
| Ph$_3$SnCNZnCl$_2$ | Me$_3$SnSbF$_6$ | .51 > .24 | .49 < 3.11 |
| Ph$_3$SnCNZnCl$_2$ | Ph$_3$SnO$_3$SCF$_3$ | .51 > .20 | .49 < 3.89 |
| Ph$_3$SnCNZnCl$_2$ | (FC$_6$H$_4$)$_3$SnSbF$_6$ | .51 > .13 | .49 < 3.90 |
| Ph$_3$SnCNZnCl$_2$ | Ph$_3$SnSbF$_6$ | .51 > .11 | .49 < 2.57 |
| Ph$_3$SnCNZnCl$_2$ | AlEtCl$_2$ | .51 > .01 | .49 < 1.88 |
| Ph$_3$SnCNZnCl$_2$ | AlCl$_3$ | .51 > .00 | .49 < 1.50 |
| (iPr)$_3$SnSbF$_6$ | (cC$_6$H$_{11}$)$_3$SnSbF$_6$ | .50 > .43 | 2.20 < 2.69 |
| (iPr)$_3$SnSbF$_6$ | (neC$_5$H$_{11}$)$_3$SnSbF$_6$ | .50 > .37 | 2.20 < 2.84 |
| (iPr)$_3$SnSbF$_6$ | ET$_3$SnSbF$_6$ | .50 > .31 | 2.20 < 2.54 |
| (iPr)$_3$SnSbF$_6$ | (iBu)$_3$SnSbF$_6$ | .50 > .29 | 2.20 < 2.65 |
| (iPr)$_3$SnSbF$_6$ | AlEt$_2$Cl | .50 > .26 | 2.20 < 2.39 |
| (iPr)$_3$SnSbF$_6$ | Me$_3$SnSbF$_6$ | .50 > .24 | 2.20 < 3.11 |
| (iPr)$_3$SnSbF$_6$ | Ph$_3$SnO$_3$SCF$_3$ | .50 > .20 | 2.20 < 3.89 |
| (iPr)$_3$SnSbF$_6$ | (FC$_6$H$_4$)$_3$SnSbF$_6$ | .50 > .13 | 2.20 < 3.90 |
| (iPr)$_3$SnSbF$_6$ | Ph$_3$SnSbF$_6$ | .50 > .11 | 2.20 < 2.57 |
| (cC$_6$H$_{11}$)$_3$SnSbF$_6$ | (neC$_5$H$_{11}$)$_3$SnSbF$_6$ | .43 > .37 | 2.69 < 2.84 |
| (cC$_6$H$_{11}$)$_3$SnSbF$_6$ | Me$_3$SnSbF$_6$ | .43 > .24 | 2.69 < 3.11 |
| (cC$_6$H$_{11}$)$_3$SnSbF$_6$ | Ph$_3$SnO$_3$SCF$_3$ | .43 > .20 | 2.69 < 3.89 |
| (cC$_6$H$_{11}$)$_3$SnSbF$_6$ | (FC$_6$H$_4$)$_3$SnSbF$_6$ | .43 > .13 | 2.69 < 3.90 |
| ZnCl$_2$ | (neC$_5$H$_{11}$)$_3$SnSbF$_6$ | .39 > .37 | .44 < 2.84 |
| ZnCl$_2$ | Et$_3$SnSbF$_6$ | .39 > .31 | .44 < 2.54 |
| ZnCl$_2$ | (iBu)$_3$SnSbF$_6$ | .39 > .29 | .44 < 2.65 |

TABLE 4-continued
Synergistic Combinations

| | | $k_1 \times 10^4$ (sec$^{-1}$) | $k_2 \times 10^3$ (sec$^{-1}$) |
|---|---|---|---|
| ZnCl$_2$ | AlEt$_2$Cl | .39 > .26 | .44 < 2.39 |
| ZnCl$_2$ | Me$_3$SnSbF$_6$ | .39 > .24 | .44 < 3.11 |
| ZnCl$_2$ | Ph$_3$SnO$_3$SCF$_3$ | .39 > .20 | .44 < 3.89 |
| ZnCl$_2$ | (FC$_6$H$_4$)$_3$SnSbF$_6$ | .39 > .13 | .44 < 3.90 |
| ZnCl$_2$ | Ph$_3$SnSbF$_6$ | .39 > .11 | .44 < 2.57 |
| ZnCl$_2$ | AlEtCl$_2$ | .39 > .01 | .44 < 1.88 |
| ZnCl$_2$ | AlCl$_3$ | .39 > .00 | .44 < 1.50 |
| (neC$_5$H$_{11}$)$_3$SnSbF$_6$ | Me$_3$SnSbF$_6$ | .37 > .24 | 2.84 < 3.11 |
| (neC$_5$H$_{11}$)$_3$SnSbF$_6$ | Ph$_3$SnO$_3$SCF$_3$ | .37 > .20 | 2.84 < 3.89 |
| (neC$_5$H$_{11}$)$_3$SnSbF$_6$ | (FC$_6$H$_4$)$_3$SnSbF$_6$ | .37 > .13 | 2.84 < 3.90 |
| Et$_3$SnSbF$_6$ | (iBu)$_3$SnSbF$_6$ | .31 > .29 | 2.54 < 2.65 |
| Et$_3$SnSbF$_6$ | Me$_3$SnSbF$_6$ | .31 > .24 | 2.54 < 3.11 |
| Et$_3$SnSbF$_6$ | Ph$_3$SnO$_3$SCF$_3$ | .31 > .20 | 2.54 < 3.89 |
| Et$_3$SnSbF$_6$ | (FC$_6$H$_4$)$_3$SnSbF$_6$ | .31 > .13 | 2.54 < 3.90 |
| Et$_3$SnSbF$_6$ | Ph$_3$SnSbF$_6$ | .31 > .11 | 2.54 < 2.57 |
| (iBu)$_3$SnSbF$_6$ | Me$_3$SnSbF$_6$ | .29 > .24 | 2.65 < 3.11 |
| (iBu)$_3$SnSbF$_6$ | Ph$_3$SnO$_3$SCF$_3$ | .29 > .20 | 2.65 < 3.89 |
| (iBu)$_3$SnSbF$_6$ | (FC$_6$H$_4$)$_3$SnSbF$_6$ | .29 > .13 | 2.65 < 3.90 |
| AlEt$_2$Cl | Me$_3$SnSbF$_6$ | .26 > .24 | 2.39 < 3.11 |
| AlEt$_2$Cl | Ph$_3$SnO$_3$SCF$_3$ | .26 > .20 | 2.39 < 3.89 |
| AlEt$_2$Cl | (FC$_6$H$_4$)$_3$SnSbF$_6$ | .26 > .13 | 2.39 < 3.90 |
| AlEt$_2$Cl | Ph$_3$SnSbF$_6$ | .26 > .11 | 2.39 < 2.57 |
| Me$_3$SnSbF$_6$ | Ph$_3$SnO$_3$SCF$_3$ | .24 > .20 | 3.11 < 3.89 |
| Me$_3$SnSbF$_6$ | (FC$_6$H$_4$)$_3$SnSbF$_6$ | .24 > .13 | 3.11 < 3.90 |
| Ph$_3$SnO$_3$SCF$_3$ | (FC$_6$H$_4$)$_3$SnSbF$_6$ | .24 > .13 | 3.89 < 3.90 |
| FeCl$_3$ | CoI$_2$ | .15 > .14 | .14 < .38 |
| FeCl$_3$ | (FC$_6$H$_4$)$_3$SnSbF$_6$ | .15 > .13 | .14 < 3.90 |
| FeCl$_3$ | Ph$_3$SnSbF$_6$ | .15 > .11 | .14 < 2.57 |
| FeCl$_3$ | TiCl$_3$ | .15 > .06 | .14 < .16 |
| FeCl$_3$ | AlEtCl$_2$ | .15 > .01 | .14 < 1.88 |
| FeCl$_3$ | AlCl$_3$ | .15 > .00 | .14 < 1.50 |
| CoI$_2$ | (FC$_6$H$_4$)$_3$SnSbF$_6$ | .14 > .13 | .38 < 3.90 |
| CoI$_2$ | Ph$_3$SnSbF$_6$ | .14 > .11 | .38 < 2.57 |
| CoI$_2$ | AlEtCl$_2$ | .14 > .01 | .38 < 1.88 |
| CoI$_2$ | AlCl$_3$ | .14 > .00 | .38 < 1.50 |
| CrCl$_2$ | (FC$_6$H$_4$)$_3$SnSbF$_6$ | .14 > .13 | .11 < 3.90 |
| CrCl$_2$ | Ph$_3$SnSbF$_6$ | .14 > .11 | .11 < 2.57 |
| CrCl$_2$ | TiCl$_3$ | .14 > .06 | .11 < .16 |
| CrCl$_2$ | AlEtCl$_2$ | .14 > .01 | .11 < 1.88 |
| CrCl$_2$ | AlCl$_3$ | .14 > .00 | .11 < 1.50 |
| Co(NO$_3$)$_2$.6H$_2$O | TiCl$_3$ | .09 > .06 | .11 < .16 |
| Co(NO$_3$)$_2$.6H$_2$O | AlEtCl$_2$ | .09 > .01 | .11 < 1.88 |
| Co(NO$_3$)$_2$.6H$_2$O | AlCl$_3$ | .09 > .00 | .11 < 1.50 |
| CrCl$_3$ | TiCl$_3$ | .08 > .06 | .10 < .16 |
| CrCl$_3$ | AlEtCl$_2$ | .08 > .01 | .10 < 1.88 |
| CrCl$_3$ | AlCl$_3$ | .08 > .00 | .10 < 1.50 |
| AlEt$_3$ | TiCl$_3$ | .07 > .06 | .10 < .16 |
| AlEt$_3$ | AlEtCl$_2$ | .07 > .01 | .10 < 1.88 |
| AlEt$_3$ | AlCl$_3$ | .07 > .00 | .10 < 1.50 |
| VCl$_3$ | TiCl$_3$ | .07 > .06 | .07 < .16 |
| VCl$_3$ | ZnMe$_2$ | .07 > .04 | .07 < .08 |
| VCl$_3$ | AlEtCl$_2$ | .07 > .01 | .07 < 1.88 |
| VCl$_3$ | AlCl$_3$ | .07 > .00 | .07 < 1.50 |
| TiCl$_3$ | AlEtCl$_2$ | .06 > .01 | .16 < 1.88 |
| TiCl$_3$ | AlCl$_3$ | .06 > .00 | .16 < 1.50 |
| FeCl$_2$.4H$_2$O | ZnMe$_2$ | .06 > .04 | .06 < .08 |
| FeCl$_2$.4H$_2$O | ZnPh$_2$ | .06 > .03 | .06 < .07 |
| FeCl$_2$.4H$_2$O | AlEtCl$_2$ | .06 > .01 | .06 < 1.88 |
| FeCl$_2$.4H$_2$O | AlCl$_3$ | .06 > .00 | .06 < 1.50 |
| ZnMe$_2$ | AlEtCl$_2$ | .04 > .01 | .08 < 1.88 |
| ZnMe$_2$ | AlCl$_3$ | .04 > .00 | .08 < 1.50 |
| ZnPh$_2$ | AlEtCl$_2$ | .03 > .01 | .07 < 1.88 |
| ZnPh$_2$ | AlCl$_3$ | .03 > .00 | .07 < 1.50 |

The Examples which follow confirm and illustrate this.

EXAMPLES 1–14
PRODUCTION OF ADN

All Examples 1–14 below were carried out as single-stage continuous hydrocyanations in a 25 mL glass, continuous, stirred-tank reactor (CSTR). The ingredients were fed from ISCO 314 pump reservoirs and products collected from the reactor overflow for analysis. Catalyst solutions were made up to 6.5–7.5:1 TTP:Ni(0) from Ni(m,p-TTP)$_4$ and m,p-TTP in 3PN (where m,p-TTP refers to tritolylphosphite with a mixture of meta and para tolyl groups). Hydrogen cyanide (purified by distillation) and promoters were fed as concentrated solutions in dried 3-pentenenitrile.

The reactions were monitored by periodic sampling of the reactor for HCN concentration; lower HCN concentration indicates higher activity. The reactions were run for 2 to 4 days to prove stability under steady state conditions. Product analysis was carried out by gas chromatography. Purified acetone was used to homogenize product mixtures which upon cooling showed phase separation, as in the high conversion examples illustrated in Table 3.

Tables 5 and 6 contain the summarized results for low conversion (50% 3,4PN→DN, DN=dinitrile) (Example 1-10), and higher conversion (70-85% 3,4PN→DN) (Examples 11-14), respectively. Synergism in a promoter combination is indicated by a steady state HCN concentration which is lower than that found for use of either promoter alone. "AF Cycles" refers to the number of moles of 3,4PN per moles of promoter fed to the reactor (sum of both promoters where more than one used); a larger number means less promoter was fed to the reactor. Yields are defined as follows:

$$\% \ ADN \ \text{Yield} = \frac{\text{Moles of } ADN \text{ produced}}{\text{Moles of } 3,4PN \text{ reacted}} \times 10^2$$

$$\% \ 2PN \ \text{Yield} = \frac{\text{Moles of } 2PN \text{ produced}}{\text{Moles of } 3,4PN \text{ reacted}} \times 10^2$$

EXAMPLE 1

A 25 mL multineck glass reactor charged with a Ni(TTP)$_4$/TTP catalyst mixture (3.62 g; about 6.6:1 TTP/Ni(0), B(C$_6$H$_5$)$_3$ (0.21 g), 3,4-pentenenitrile (PN's) (9.25 g), and adiponitrile (9.44 g) was warmed to and maintained at 50° C. with a thermostatically controlled heated air gun. The following solutions (wt %) were fed from reservoir pumps in a continuous fashion for 48.6 hours:

| Solution | Feed Rate |
|---|---|
| Catalyst/TTP/PN's; 1.17% Ni(0), 6.6:1 TTP:Ni(0) | 1.577 g/hr |
| HCN/PN's; 18.5% HCN | 2.318 g/hr |
| BPh$_3$/PN's; 20.0% BPh$_3$ | 0.192 g/hr |

Product receivers were changed periodically to facilitate sampling. The productivity of the reaction was 0.55 lb of adiponitrile/gallon-hour. HCN concentration was monitored periodically by measuring the cyanide absorption at 2095 cm$^{-1}$ by calibrated infrared spectroscopy in a CaF$_2$ cell. The reaction achieved a steady state level of HCN as indicated in Table 5 along with the corresponding product yields.

EXAMPLES 2-10

These were carried out in the manner of Example 1 except that where two promoters were used, an additional solution was prepared and fed simultaneously.

EXAMPLE 11

A 25 mL multineck glass reactor charged with Ni(TTP)$_4$/TTP catalyst mixture (5.53 g; about 6.6:1 TTP:Ni(0)), Ph$_3$SnOTf (OTf=CF$_3$SO$_3$) (0.72 g, 98.4% purity), 3,4-pentenenitrile (PN's) (2.50 g) and adiponitrile (14.50 g) was warmed to and maintained at 60° C. with a thermostatically controlled heated air gun. The following solutions (wt %) were fed from ISCO reservoir pumps in a continuous fashion for 51.7 hours (6.8 reactor turnovers) with product overflowing into an ambient temperature receiver bottle:

| Solution | Feed Rate |
|---|---|
| Catalyst/TTP/PN's; 1.87% Ni(0), 78.68% TTP (7.0:1 TTP:Ni(0)), 14.68% PN's | 0.848 g/hr |
| HCN/PN's; 32.0% HCN | 1.577 g/hr |
| Ph$_3$SnOTf/PN's; 21.98% Ph$_3$SnOTf | 0.434 g/hr |
| 3,4-PN's | 0.296 g/hr |

Product receivers were changed periodically to facilitate sampling. The reactor solution HCN concentration was monitored as in Example 1. On cooling, the overflow product separated into two phases; this mixture was homogenized by addition of a small amount of purified acetone and analyzed by gc, 1c, and emission spectroscopy to give the results shown in Table 6.

EXAMPLES 12-14

These were carried out in the manner described in Example 12, except where two promoters were used an additional solution was prepared and fed simultaneously.

TABLE 5

LOW CONVERSION HYDROCYANATIONS[a]

| Example # or Comp. Ex. #/ Promoter(s) | Mole Ratio of Promoters | AF Cycles | HCN Concentration ppm | % ADN Yield | % 2PN Yield |
|---|---|---|---|---|---|
| 1a/BPh$_3$ | — | 100 | 290 | 91.7 | 4.5 |
| 1b/BPh$_3$ | — | 200 | >5000 | Rxn Failed | |
| 2/Ph$_3$SnOTf | — | 197 | 1274 | 83.8 | 1.2 |
| 3a/BPh$_3$ + Ph$_3$SnOTf | 1.1:1 | 191 | 185 | 87.3 | 1.5 |
| 3b/BPh$_3$ + Ph$_3$SnOTf | 3.1:1 | 188 | 247 | 89.5 | 2.4 |
| 3c/BPh$_3$ + Ph$_3$SnOTf | 3.3:1 | 268 | 553 | 89.3 | 2.3 |
| 4/Ph$_3$SnPh$_3$BCN | — | 210 | 1373 | 84.9 | 1.2 |
| 5a/BPh$_3$ + Ph$_3$SnPh$_3$BCN | 2.8:1 | 201 | 272 | 89.9 | 2.6 |
| 5b/BPh$_3$ + Ph$_3$SnPh$_3$BCN | 5.0:1 | 191 | 339 | 90.8 | 3.6 |
| 6/Cy$_3$SnOTf | — | 194 | 445 | 90.1 | 1.9 |
| 7/BPh$_3$ + Cy$_3$SnOTf | 10:1 | 190 | 267 | 90.3 | 2.5 |
| 8/ZnCl$_2$ | — | 207 | 264 | 81.7 | 1.8 |
| 9/BPh$_3$ + ZnCl$_2$ | 0.9:1 | 191 | 379 | 82.0 | 2.3 |
| 10/ZnCl$_2$ + Ph$_3$SnOTf | 1.0:1 | 199 | 5 | 78.0 | 1.2 |

OTf = O$_3$SCF$_3$; Cy = C$_6$H$_{11}$; Ph = C$_6$H$_5$.
[a]Reactions at 0.55 lb ADN/gal.-hr., 50° C., 50 AF cycles Ni(O), 50% 3,4PN → DN conversion

TABLE 6

HIGH CONVERSION HYDROCYANATIONS[a]

| Example #/ Promoter(s) | Mole Ratio of Promoters | AF Cycles Promoters | HCN Concentration ppm | % ADN Yield | % 2PN Yield |
| --- | --- | --- | --- | --- | --- |
| 11/Ph$_3$SnO$_3$SCF$_3$ | — | 97 | 771 | 82.5 | 0.5 |
| 12a/Ph$_3$B + Ph$_3$SnO$_3$SCF$_3$ | 2.6:1 | 98 | 274 | 83.8 | 1.1 |
| 12b/Ph$_3$B + Ph$_3$SnO$_3$SCF$_3$ | 9.5:1 | 102 | 1017 | 87.8 | 1.8 |
| 12c/Ph$_3$B + Ph$_3$SnO$_3$SCF$_3$ | 3.1:1 (50° C.) | 98 | 1332 | 85.6 | 1.0 |
| 13a/Ph$_3$B + Ph$_3$SnPh$_3$BCN | 7.5:1 | 98 | 565 | 88.3 | 2.2 |
| 13b/Ph$_3$B + Ph$_3$SnPh$_3$BCN | 19.1:1 (70% conv.) | 99 | 286 | 90.3 | 4.5 |
| 14a/Ph$_3$B + Cy$_3$SnO$_3$SCF$_3$ | 2.6:1 | 97 | 830 | 91.0 | 2.0 |
| 14b/Ph$_3$B + Cy$_3$SnO$_3$SCF$_3$ | 5.3:1 (72% conv., ⅔ rate) | 97 | 158 | 90.1 | 3.6 |

[a]Reactions at 0.55 lb ADN/gal-hr, 60° C., 67 AF cycles Ni(O), 85% 3,4PN → DN conversion unless otherwise noted

What is claimed:

1. In a process for producing adiponitrile by the addition of hydrogen cyanide to pentenenitriles in the presence of a zerovalent nickel catalyst and catalyst promoter, the improvement comprising conducting the process in the presence of a combination of two Lewis acid promoters, $LA_A$ and $LA_B$, wherein the rate constant for the rate of isomerization of 3-pentenenitrile to 4-pentenenitrile, $k_1$, in the presence of the first Lewis acid promoter, $LA_A$ is greater than $k_1$ in the presence of the second Lewis acid promoter, $LA_B$, and wherein the rate constant for the rate of hydrocyanation of 4-pentenenitrile to adiponitrile, $k_2$, in the presence of $LA_B$ is greater than $k_2$ in the presence of $LA_A$.

2. The process of claim 1 wherein $LA_A$ is BPH$_3$ and $LA_B$ is one selected from CoCl$_2$, ZnI$_2$, AlCl$_3$, AlRCl$_2$, AlR$_2$Cl, R$_3$SnX, Ar$_3$SnY, where R is an alkyl group of from 1 to 15 carbons, Ar is a substituted or non-substituted aryl group of from 1 to 20 carbons, X is selected from SbF$_6$, PF$_6$, BF$_4$, or CF$_3$SO$_3$, and Y is selected from SbF$_6$, PF$_6$, BF$_4$, CF$_3$SO$_3$, or Ph$_3$BCN.

3. The process of claim 1 wherein $LA_A$ is one selected from CoCl$_2$, ZnI$_2$, Ph$_3$SnPh$_3$BCN, or Ph$_3$SnZnCl$_2$CN and $LA_B$ is one selected from AlCl$_3$, AlRCl$_2$, AlR$_2$Cl, R$_3$SnX', Ar$_3$SnY', where R is an alkyl group of from 1 to 15 carbons, Ar is a substituted or non-substituted aryl group of from 1 to 20 carbons, X' is selected from SbF$_6$, PF$_6$, or BF$_4$, and Y' is selected from SbF$_6$, PF$_6$, BF$_4$, CF$_3$SO$_3$.

4. The process of claim 1 wherein $LA_A$ is ZnCl$_2$ and $LA_B$ is one selected from AlCl$_3$, AlRCl$_2$, AlR$_2$Cl, R$_3$SnX', Ar$_3$SnY' where R is an alkyl group of from 1 to 15 carbons, Ar is a substituted or non-substituted aryl group of from 1 to 20 carbons, X' is selected from SbF$_6$, PF$_6$, or BF$_4$, and Y' is selected from SbF$_6$, PF$_6$, BF$_4$, CF$_3$SO$_3$.

5. The process of claim 1 wherein $LA_A$ is selected from AlR$_2$Cl or CoI$_2$ and $LA_B$ is Ar$_3$SnY' where R is an alkyl group of from 1 to 15 carbons, Ar is a substituted or nonsubstituted aryl group of from 1 to 20 carbons, and Y is selected from SbF$_6$, PF$_6$, BF$_4$, CF$_3$SO$_3$.

6. The process of claim 1 wherein $LA_A$ is BPh$_3$ and $LA_B$ is Ph$_3$SnPh$_3$BCN.

* * * * *

UNITED STATES PATENT AND TRADEMARK OFFICE
CERTIFICATE OF CORRECTION

PATENT NO. : 4,874,884
DATED : October 17, 1989
INVENTOR(S) : Ronald J. McKinney and Robert B. Osborne It is certified that error appears in the above-identified patent and that said Letters Patent is hereby corrected as shown below:

At Column 2, line 57, delete "$R_2SnX$" and insert in its place --$R_3SnX$--.

At Column 3, line 62 delete "[3PNH]" and insert in its place --[3PN]--.

At Column 4, line 43, delete "$NiL_43PN$" and insert in its place --3PN--.

At Column 4, lines 49, delete "aryl groups", and insert in its place --aryl group--.

At Column 4, line 50 insert after "atoms)", --containing--.

At Column 4, line 68, delete "with aryl".

At Column 5, line 4, delete "$NiL4$" and insert in its place --$NiL_4$--.

At Column 13, line 40 delete "$BPH_3$" and insert in its place --$BPh_3$--.

At Column 14, line 43 delete "Y" and insert in its place --Y'--.

Signed and Sealed this

Tenth Day of September, 1991

*Attest:*

HARRY F. MANBECK, JR.

*Attesting Officer*   *Commissioner of Patents and Trademarks*